United States Patent
Dilger (10) Patent No.: US 6,408,674 B1
(45) Date of Patent: Jun. 25, 2002

(54) PRESSURE ACTIVATED CALIBRATION SYSTEM FOR CHEMICAL SENSORS

(75) Inventor: John Patrick Dilger, Marshalltown, IA (US)

(73) Assignee: Fisher Controls International, Austin, TX (US)

( * ) Notice: Subject to any disclaimer, the term of this patent is extended or adjusted under 35 U.S.C. 154(b) by 0 days.

(21) Appl. No.: 09/287,245

(22) Filed: Apr. 7, 1999

(51) Int. Cl.[7] ................................................ G01N 21/00
(52) U.S. Cl. ........................... 73/1.02; 73/1.05; 73/1.19
(58) Field of Search ................................. 73/1.02, 1.03, 73/1.04, 1.05, 1.06, 1.19

(56) References Cited

U.S. PATENT DOCUMENTS

| | | |
|---|---|---|
| 3,290,920 A | 12/1966 | Novak |
| 3,516,278 A | 6/1970 | Klein et al. |
| 3,760,773 A | 9/1973 | Christensen |
| 4,064,572 A * | 12/1977 | Wicks, III et al. ............... 4/227 |
| 4,164,861 A | 8/1979 | Schlereth et al. |
| 4,172,378 A | 10/1979 | Limp |
| 4,343,176 A | 8/1982 | Basford et al. |
| 4,462,760 A | 7/1984 | Sarich et al. |
| 4,554,945 A | 11/1985 | McKay |
| 4,713,618 A | 12/1987 | Carlson et al. |
| 4,742,708 A | 5/1988 | Porter |
| 5,028,394 A | 7/1991 | Lowell, Jr. et al. |
| 5,094,958 A | 3/1992 | Klainer et al. |
| 5,185,263 A | 2/1993 | Kroneis et al. |
| 5,262,127 A | 11/1993 | Wise et al. |
| 5,363,689 A | 11/1994 | Hoffmann et al. |
| 5,385,709 A | 1/1995 | Wise et al. |
| 5,447,688 A | 9/1995 | Moore |
| 5,493,890 A | 2/1996 | Dussault et al. |
| 5,550,053 A | 8/1996 | Salpeter |
| 5,970,778 A * | 10/1999 | Dilger ........................ 73/1.05 |

FOREIGN PATENT DOCUMENTS

GB    1178202    1/1970

OTHER PUBLICATIONS

International Seacrh Report, PCT Appl. No. PCT/US00/07943 mailed Jun. 16, 2000.
PCT Written Opinion, PCT. Appl. No. PCT/US00/07943, Failed Feb. 20, 2001.

* cited by examiner

Primary Examiner—Hezron Williams
Assistant Examiner—Michael Cygan
(74) Attorney, Agent, or Firm—Marshall, Gerstein & Borun

(57) ABSTRACT

A device for remotely calibrating leak sensors is disclosed. The leak sensor calibration device includes a reservoir for storing a fluid calibrant, a conduit in flow communication with the reservoir, an outlet nozzle, an air supply source, and a valve mechanism. A portion of the conduit defines a dosing chamber for storing a measured quantity of the calibrant, and the outlet nozzle is in flow communication with the dosing chamber. The air supply source is adapted to pressurize the measured quantity of calibrant stored in the dosing chamber. The valve mechanism is adapted to eject the measured quantity of calibrant stored in the dosing chamber to the atmosphere through the outlet nozzle.

7 Claims, 5 Drawing Sheets

PRESSURE ACTIVATED CALIBRATION SYSTEM FOR CHEMICAL SENSORS

FIELD OF THE INVENTION

The present invention relates to a calibration system for chemical sensors. More specifically, the present invention relates to a pressure actuated calibration device which delivers a metered dose of calibrant to the atmosphere from a dosing chamber.

BACKGROUND OF THE INVENTION

Industrial manufacturing, processing and storage facilities such as chemical plants, refineries and shipping terminals typically include a vast network of piping systems for transporting the raw or finished products through the facility. Such piping systems necessarily include a number of valves for controlling the flow of material through the facility.

Many of the products handled in the aforementioned plants are hazardous volatile organic compounds (VOC's). Unfortunately, the valves used to control the flow of material through the plants typically experience a certain amount of undesired leakage referred to as "fugitive" emissions. Fugitive emissions, which are regulated by the Environmental Protection Agency (EPA), frequently occur around the packing between the valve stem and the body of the valve. These fugitive emissions must be monitored in order to comply with EPA emission regulations. Accordingly, leak detectors are placed near the valves, usually adjacent to the leak prone valve stems or other non-point sources, in order to monitor the leakage rate.

In order to obtain accurate readings, the leak detectors must be calibrated on a periodic basis, which typically must be accomplished from a remote location. One method of calibrating such leak detectors is to eject a small quantity of calibrant adjacent to the leak detector. The detector reading is then compared to a standard based on empirical data or a look up table, and the detector is adjusted accordingly.

SUMMARY OF THE INVENTION

In accordance with a first aspect of the invention, a leak sensor calibration device comprises a reservoir for storing a calibrant, a conduit in flow communication with the reservoir, an outlet nozzle, an air supply source, and a valve mechanism. A portion of the conduit defines a dosing chamber for storing a measured quantity of the calibrant, and the outlet nozzle is in flow communication with the dosing chamber. The air supply source is adapted to pressurize the measured quantity of calibrant stored in the dosing chamber. The valve mechanism is adapted to eject the measured quantity of calibrant stored in the dosing chamber to the atmosphere through the outlet nozzle.

In further accordance with a preferred embodiment of the invention, a flow restrictor is disposed between the dosing chamber and the reservoir. The flow restrictor may be a bi-stable check valve. Alternatively, the conduit may include a portion adapted to hold a second quantity of calibrant, with the second quantity of calibrant being greater than the measured quantity of calibrant. The conduit portion is disposed between the dosing chamber and the reservoir and thus forms a pneumatic restrictor.

The valve mechanism preferably includes a first remotely operable valve disposed between the dosing chamber and the outlet nozzle. The valve mechanism preferably also includes a second remotely operable valve disposed between the air supply source and the dosing chamber. The first valve is shiftable between a closed position and an open position. When in the closed position, the first valve isolates the dosing chamber from the outlet nozzle. The second valve is shiftable between a closed position and an open position. When in the closed position the second valve isolates the air supply source from the dosing chamber. A check valve may be disposed between the dosing chamber and the reservoir, with the check valve being shiftable between an open position and a closed position. The check valve is shiftable toward its closed position in response to movement of the second valve toward the open position.

The first and second valves are preferably electrical remotely operable valves, and are operably connected to a controller for remotely operating the first and second valves. Preferably, the controller is adapted to move the first valve to the open position for a first predetermined time interval, and to move the second valve to the open position for a second predetermined time interval. Still preferably, the second time interval is less than the first time interval and occurs during the first time interval. The first time interval may be approximately 50 milliseconds, while the second time interval may be approximately 10 milliseconds. As a precondition, the controller may move the second valve to the open position for a third predetermined time interval prior to the first and second time intervals. This precondition refills the dosing chamber more effectively.

In accordance with a second aspect of the invention, a leak sensor calibrating device for delivering a metered quantity of vaporized material to the surrounding atmosphere comprises a reservoir for storing the material, an outlet nozzle, a conduit providing flow communication between the reservoir and the outlet nozzle, a pressure source, and a valve system adapted to communicate the pressure source to the dosing chamber. The conduit includes a first portion defining a dosing chamber for storing the metered quantity of the material and also including a second portion disposed between the dosing chamber and the reservoir. The conduit second portion is adapted to impede the flow of the metered quantity back toward the reservoir. By operation of the valve system, the device ejects the metered quantity stored in the dosing chamber through the outlet nozzle to the atmosphere.

According to yet another aspect of the invention, a leak sensor calibrating device includes a reservoir for storing a fluid calibrant, and a conduit in flow communication with the storage reservoir. The conduit terminates in an outlet nozzle and includes a central portion defining a dosing chamber for storing a measured quantity of the fluid calibrant. The device also includes a pressure source for pressurizing the measured quantity stored in the dosing chamber, a valve system for isolating the dosing chamber from the surrounding atmosphere, and a control system operatively connected to the valve system.

In further accordance with a preferred embodiment, the reservoir may be adapted to contain a liquid analyte calibrant, and the dosing chamber may be sized to house therein a volume in the range of two (2) microliters. The reservoir may also be adapted to house therein an analyte calibrant in a vapor phase, in which case the dosing chamber may be sized to house therein a volume in the range of five hundred (500) microliters.

According to a still further aspect of the invention, a device is provided for use on a process system having a fluid material flowing through a conduit, such that the device will eject a measured quantity of the fluid material toward a sensor. The device comprises a port in flow communication with the conduit, with a portion of the port defining a dosing chamber for storing a measured quantity of the fluid material. An outlet nozzle is in flow communication with the dosing chamber, and an air supply source provides pressure to the measured quantity of calibrant stored in the dosing chamber. A valve mechanism is provided and is adapted to eject the measured quantity of calibrant stored in the dosing chamber to the atmosphere through the outlet nozzle. Accordingly, the constituency of the fluid material may be determined by the sensor.

Further advantages and features of the present invention will become evident to those skilled in the art upon a reading of the following description.

DETAILED DESCRIPTION OF THE PREFERRED EMBODIMENT

The embodiment described herein is not intended to limit the invention to precise form disclosed. Rather, the embodiment has been chosen and described in order to enable those skilled in the art to follow the teachings of the present invention.

Figure 1:
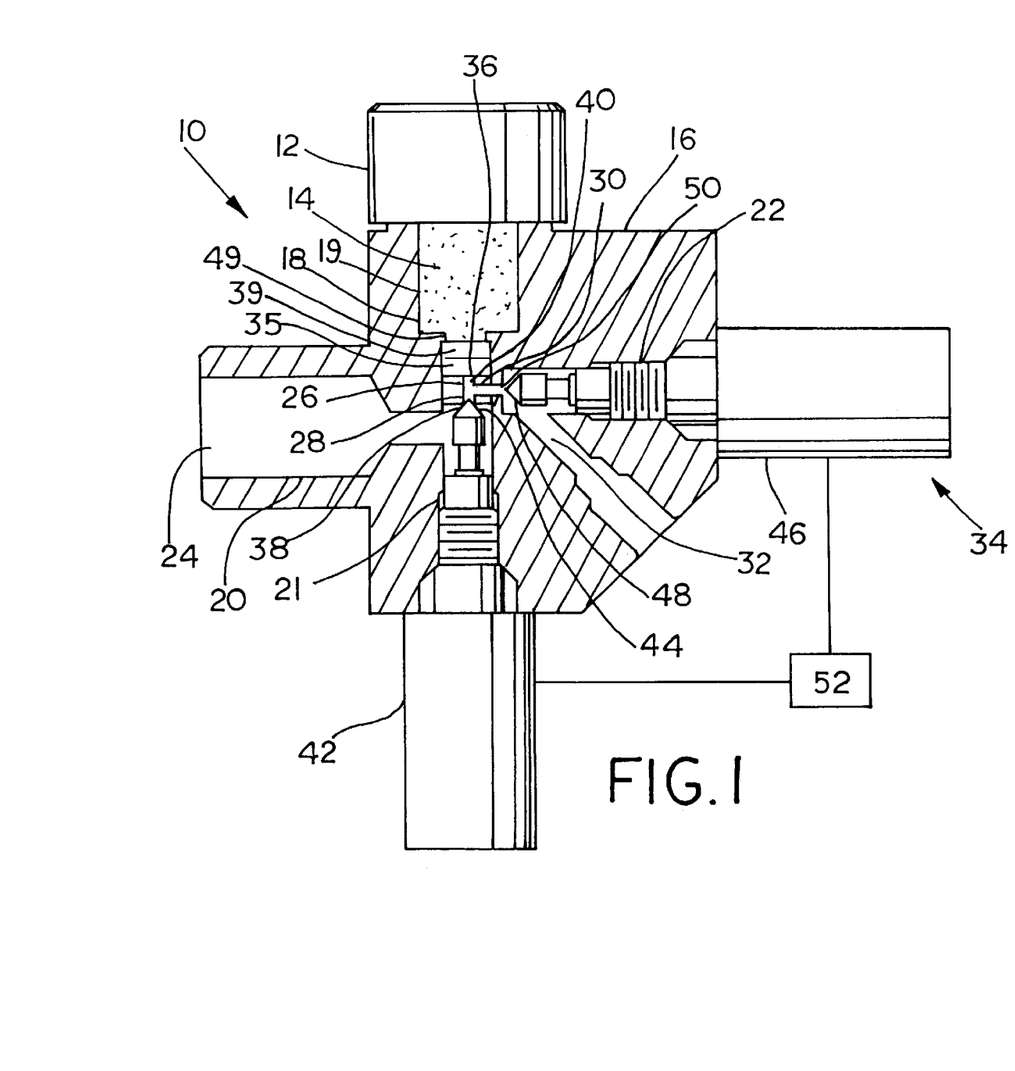
FIG. 1 is a schematic view, partly in section, of a leak sensor calibrating device constructed in accordance with the teachings of the present invention.

Referring now to FIG. 1 of the drawings, a leak sensor calibrating device constructed in accordance with the teachings of the present invention is generally referred to by the reference numeral 10. The calibrating device 10 is typically placed closely adjacent to a gas sensor array (not shown), which in turn is typically placed closely adjacent to the system which is to be monitored for leakage, such as a valve, a pipe system or seal, or any other potential emission source (not shown). The device 10 includes a reservoir 12 which contains a quantity of analyte calibrant 14, which is preferably the same material as is running through the valve or other system component (not shown) to be monitored. As explained in further detail below, the analyte calibrant 14 may be in either a liquid phase or in a vapor phase.

The device 10 includes a body or housing 16 having a plurality of intersecting conduits or bores 18, 20 and 22. The housing 16 is preferably manufactured of stainless steel or other suitable materials. The bore 18 includes first and second sections 19, 21, respectively. The bore 18 extends substantially through the housing 16 and is in flow communication with the reservoir 12 and the bore 20. The bore 20 extends to the bore 18 and is in flow communication with an outlet nozzle 24. The outlet nozzle 24 will preferably be placed closely adjacent to the valve (or other system component) to be monitored for leakage (not shown). A bore 26 connects the bores 18 and 20, and defines a dosing chamber 28. The dosing chamber 28 is preferably of a predetermined volume. For example, in the event the analyte calibrant 14 is to be utilized in a liquid phase, the volume of the dosing chamber 28 may be in the range of 2 microliters ($2 \times 10^{-6}$ cubic centimeters). By comparison, in the event the analyte calibrant 14 is to be utilized in a vapor phase, the volume of the dosing chamber 28 may be in the range of 500 microliters ($500 \times 10^{-6}$ cubic centimeters). Other volumes may be contemplated, as long as the dosing chamber 28 stores the predetermined volume of calibrant 14. The desired amount or volume of calibrant 14 to be ejected from the outlet nozzle 24 may be chosen based on a number of factors, including the type, concentration, purity, and state (i.e., liquid or vapor) of the chosen calibrant, as well as the temperature, humidity, etc. of the surrounding environment, all of which would be well known to those of skill in the art. The desired amount of calibrant 14 to be ejected can be increased or decreased by changing the volume of the dosing chamber 28.

Figure 4:
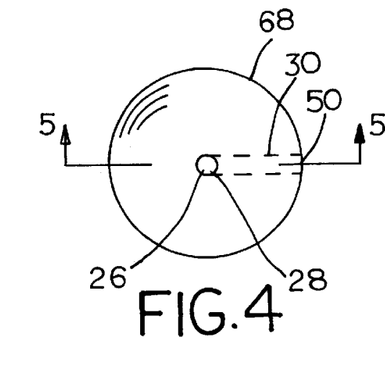
FIG. 4 is an enlarged top plan view of a Teflon insert having defined therein the dosing chamber.
Figure 5:
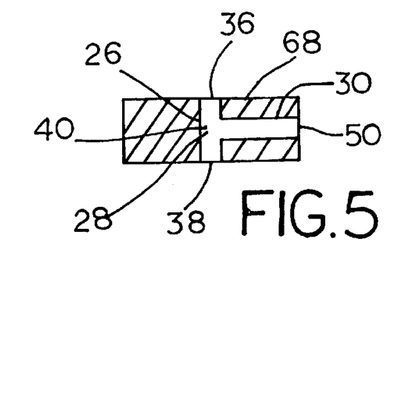
FIG. 5 is an enlarged cross-sectional view of the Teflon insert taken along line 5—5 of FIG. 4.

As shown in FIGS. 1, 4 and 5, a bore 30 connects the bore 22 with the dosing chamber 28, and an air supply inlet 32 intersects the bore 22. The air supply inlet is connected to a source of pressurized air (not shown), the purpose of which will be explained in greater detail below. Preferably, the air is supplied from the supply source at approximately 3 psig, with appropriate deviations therefrom being possible as would be contemplated by those skilled in the art. The device 10 includes a valving mechanism 34 which, as will be explained in greater detail below, is adapted to eject a desired quantity of calibrant 14 from the dosing chamber 28 through the outlet nozzle 24.

Figure 5A:
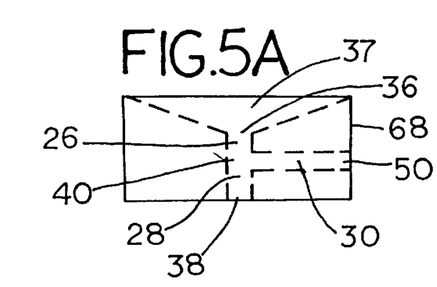
FIG. 5A is an enlarged cross-sectional view similar to FIG. 5 but illustrating a Teflon insert having a conical portion at the input side of the insert.

The dosing chamber 28 includes an input end 36, an output end 38, and an intermediate portion 40 as shown in FIG. 5. The bore 30 intersects the dosing chamber 28 at the intermediate portion 40. As shown in FIG. 5A, the input end 36 of the bore 26 may alternatively include a flared or conical portion 37.

Figure 6:
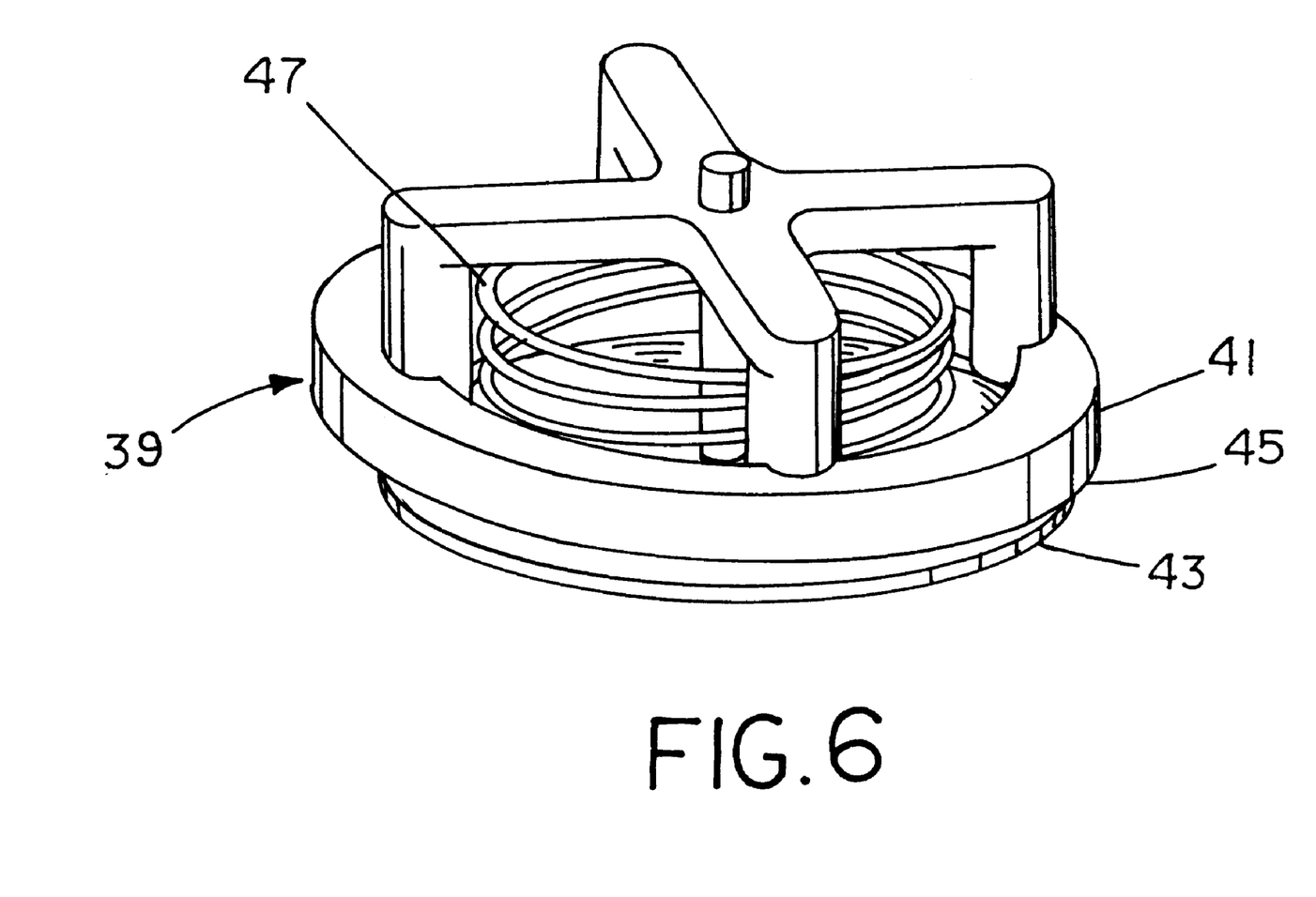
FIG. 6 is an enlarged perspective view of a check valve adapted for use with the present invention.
Figure 7:
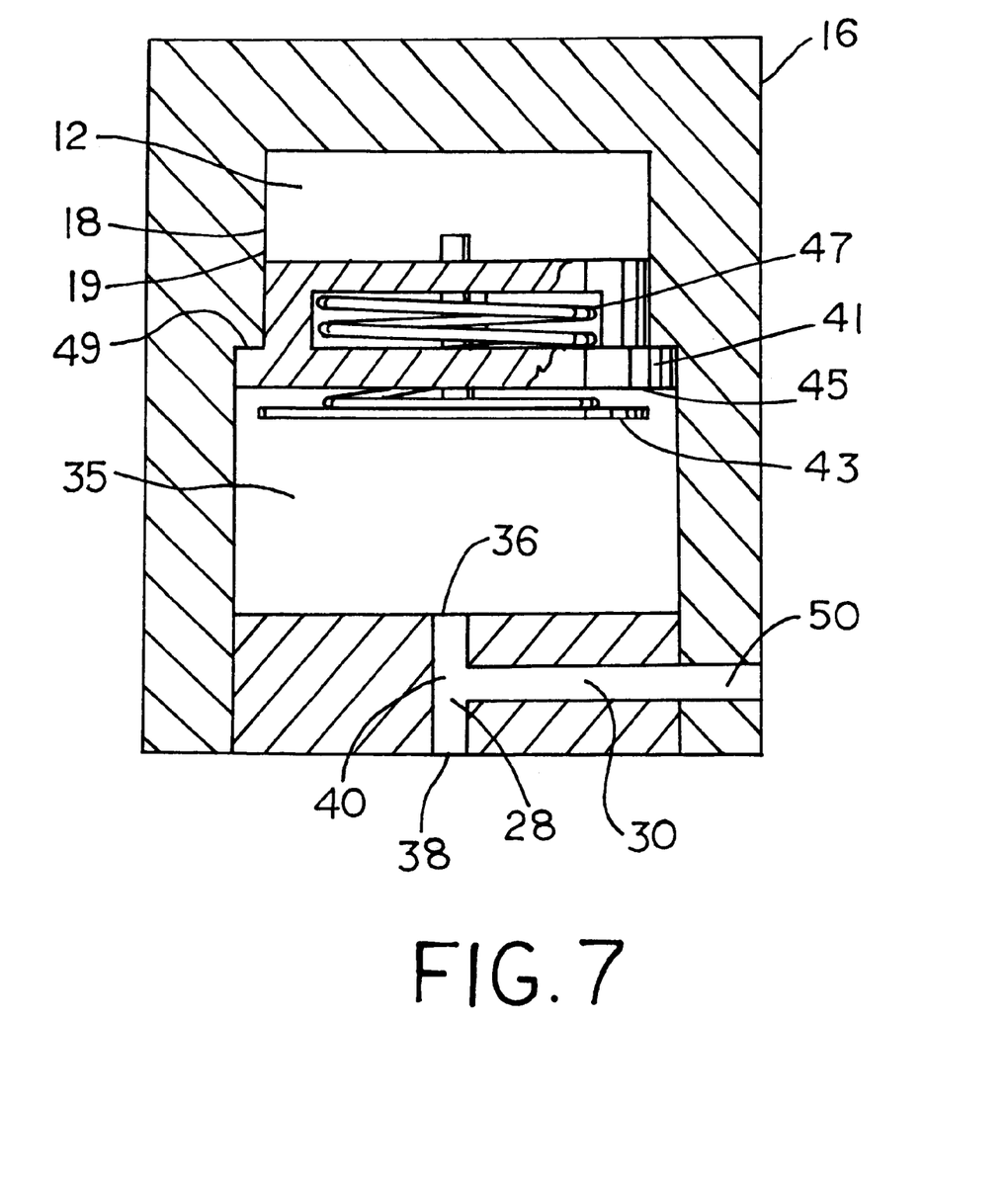
FIG. 7 is a fragmentary schematic view illustrating the position of the check valve relative to the dosing chamber and the calibrant reservoir.

As shown in FIG. 1, a check valve 39 is disposed in the portion 19 of the bore 18 generally adjacent to the input end 36 of the dosing chamber 28. Referring to FIGS. 6 and 7, the check valve 39 includes a housing 41 sized to be received in the portion 19 of the bore 21. The check valve 39 includes a plate or disc 43 which is sized to be received against a valve seat 45, and further includes a spring 47 for biasing the disc 43 toward a normally open position as shown in FIG. 7. As can be seen in FIG. 7, the portion 19 of the bore 18 may include an annular seat 49, enabling the check valve 39 to be pressed into place (for example, from below when viewing FIG. 7).

When the valving mechanism 34 is activated in the manner to be described in greater detail below, the introduction of the actuation pressure against the disc 43 causes the disk 43 to move upwardly (when viewing the Figs.) such that the disc 43 is seated against the valve seat 45. Accordingly, any flow of the calibrant 14 back toward the reservoir 12 is prevented. It will be noted that the check valve 39 is thus operated automatically in response to the operation of the valving mechanism 34, and will further behave as a bi-stable check valve. As will be noted from FIG. 7, the check valve 39 is preferably located slightly away from the input end 36 of the bore 26 so as to define a chamber 35. It will be understood that the volume of the reservoir 12 is preferably much greater than the volume of the dosing chamber 28, in order to facilitate rapid refilling of the dosing chamber 28 after the measured quantity stored therein has been ejected through the outlet nozzle. In the preferred embodiment, the volume of the reservoir 12 may be approximately twenty (20) times the volume of the dosing chamber 28.

Referring again to FIGS. 1, 2 and 3, the valve mechanism 34 includes a first valve 42 disposed in the section 21 of the bore 18. The valve 42 includes a tip 44 adapted to close off the outlet end 38 of the dosing chamber 28. The valve mechanism 34 also includes a second valve 46 disposed in the bore 22 and having a tip 48 adapted to close off an inlet end 50 of the bore 30. Each of the valves 42 and 46 is shiftable between closed and open positions. When the valve 42 is in a closed position, the valve 42 isolates the dosing chamber 28 from the outlet nozzle 24. When the valve 42 is in an open position, the dosing chamber 28 is in flow communication with the outlet nozzle 24. When the second valve 46 is in the closed position, the valve 46 isolates the air inlet 32 from the dosing chamber 28. When the valve 46 is in the open position, the air inlet 32 is in flow communication with the dosing chamber 28. Preferably, each of the valves 42 and 46 is a remotely operable, electrically actuated microvalve. Still preferably, each of the valves 42, 46 are remotely operable from a common control system 52.

Figure 2:
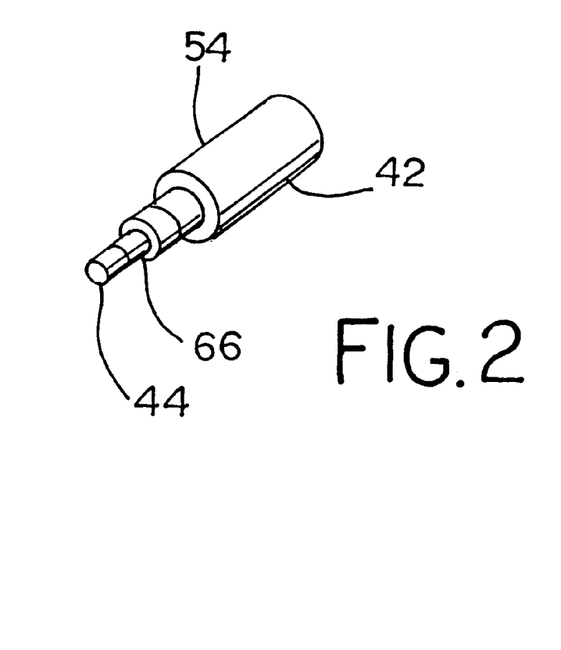
FIG. 2 is a perspective view of a remotely operable microvalve for use with a device constructed in accordance with the teachings of the present invention.
Figure 3:
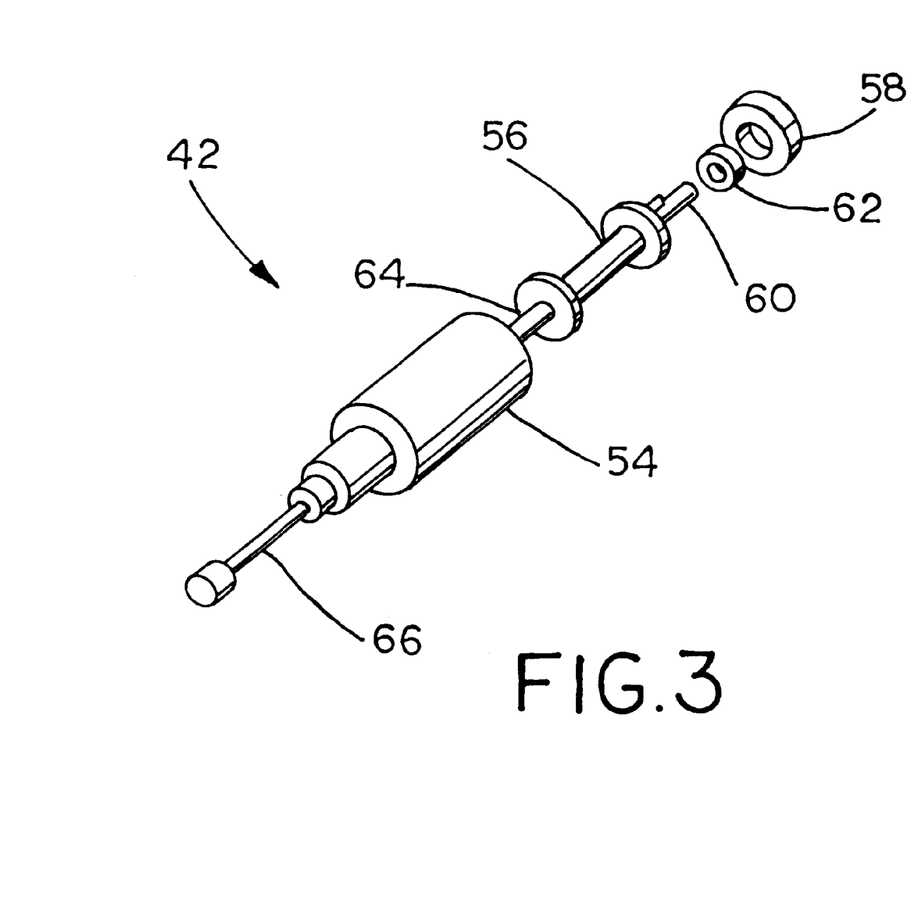
FIG. 3 is an exploded view in perspective of the microvalve shown in FIG. 2.

Referring now to FIGS. 2 and 3, the valve 42 is shown. It will be understood that the structure and operation of the valve 46 is substantially the same. However, only the structure and operation of the valve 42 will be described in detail. The valve 42 includes a body 54, an electromagnetic bobbin 56, a pair of soft magnetic pole pieces 58, 60, a rare earth permanent magnet 62 an insulator 64 and an armature 66. The valve body 54, the pole pieces 58, 60, and the armature 66 are preferably constructed using 17-4 stainless steel, while the insulator 64 is preferably constructed of 316 stainless steel. The magnet 62 is preferably constructed of Nickel Iron Boron. The valves 42 and 46 are preferably electrically operable valves, having a six (6) volt actuation energy drawing 250 mA at 10 milliseconds. Other suitable valves may be substituted.

Referring now to FIGS. 1 and 4, a Teflon® insert 68 may be used at the intersection of the bores 18, 20 and 22. The Teflon insert 68 is preferably compression molded using known techniques, so as to have defined therein the dosing chamber 28 and the bore 30. The use of a separate insert 68 greatly eases the manufacturing process by permitting the housing 16 to be manufactured to a first set of tolerances, while the insert 68 is manufactured to a second, more rigorous set of tolerances. The insert 68 also provides a better seal at the tip 44 and 48 of the valves 42 and 46, respectively.

In operation, when the device 10 is inactive, the valves 42 and 46 are both closed, and the calibrant 14 in reservoir 12 is free to flow into the dosing chamber 28 by virtue of the fact that the check valve 39 is in an open position. When it is desired to activate the device 10, the control system 52 first opens the valve 46, preferably for a period of 50 milliseconds. While the valve 46 is open, the control system 52 next opens the valve 42, which permits the pressurized air from the air source to flow through the air inlet 32. The resulting pressure increase causes the check valve 39 to immediately shift to its closed position. The incoming air acts to displace the measured quantity of calibrant 14 stored in the dosing chamber 28, causing the measured quantity to be ejected from the outlet nozzle 24. By virtue of the check valve 39 moving to its closed position upon the introduction of the actuation pressure, any flow of calibrant 14 from the dosing chamber 28 toward the reservoir 12 is prevented, and the calibrant 14 in the dosing chamber 28 is ejected out of the outlet nozzle 24. After the desired 10 millisecond interval, the valve 42 is closed. Shortly thereafter, valve 46 is closed. With the actuation pressure closed off, the check valve 39 returns to its normal open position aided by the force of the spring 47, and calibrant 14 is free to flow from the reservoir into the dosing chamber 28.

In the process, the exhausted calibrant 14 is mixed with a known quantity of atmosphere from around a process system valve (not shown) for the purpose of measuring or predicting the leak emissions from the valve. The leak sensor (not shown) can be calibrated by comparing the obtained sensor reading to empirical data, or by using other known methods.

It will be noted by those skilled in the art that it may be advantageous to use the calibrant 14 in its vapor state. When using a vaporized calibrant 14 within the device 10, the potential for leakage at each of the valves 42, 46 is greatly minimized, especially when the device 10 is used in high temperature environments. In the event a vaporized calibrant is used, the leak sensor (not shown) may be calibrated by taking into consideration the surrounding temperature and the vapor pressure of the calibrant in order to calculate the entrained quantity of calibrant ejected from the outlet nozzle 24.

It will also be noted by those skilled in the art that, using the same principles discussed hereinabove, the present device 10 may be used in order to periodically test the constituency or purity of a substance flowing through a pipeline or other conveyance in an industrial process system (not shown). In such an application, the reservoir 14 would be in constant flow communication with the substance flowing through the pipeline or system, and the outlet nozzle 24 would be placed in close proximity to an appropriate sensor.

Figure 8:
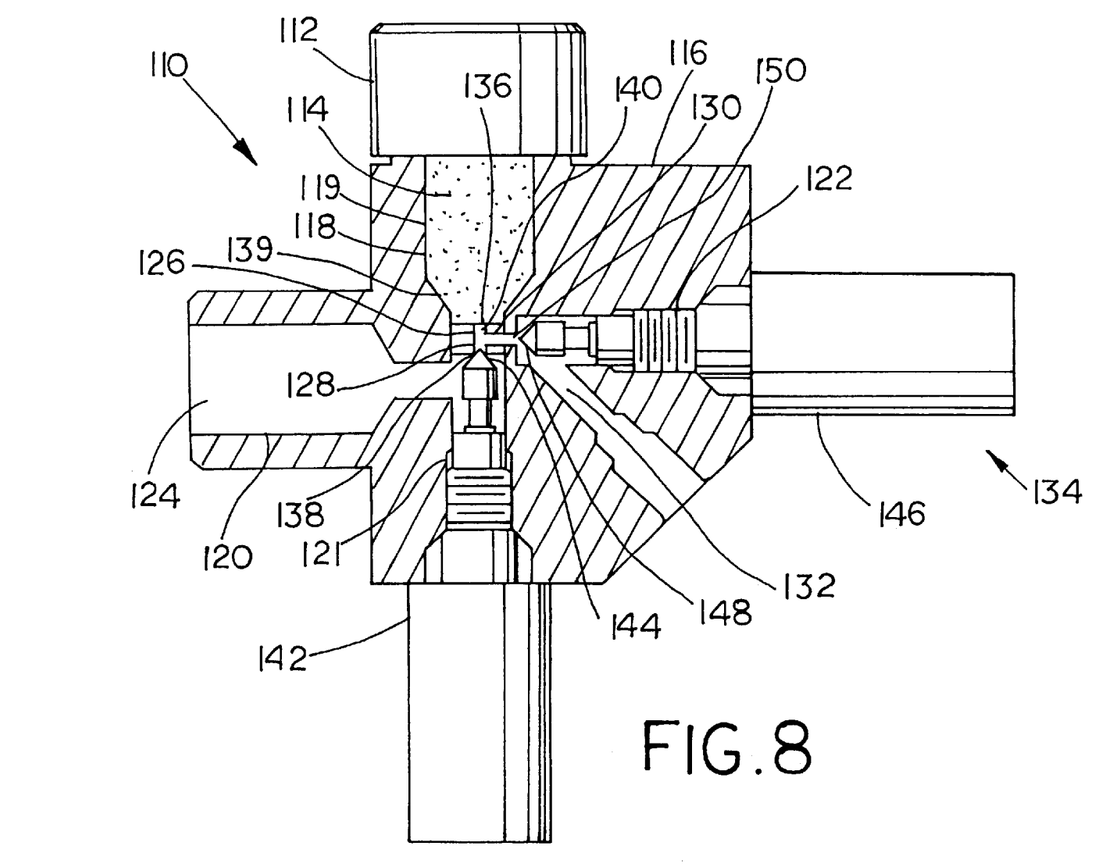
FIG. 8 is a schematic view, partly in section, similar to FIG. 1 but assembled according a second preferred embodiment of the invention.

Referring now to FIG. 8, a second preferred embodiment is shown in which all elements that are the same or similar as the embodiment discussed above will retain the same reference characters, but increased by 100. A leak sensor calibrating device 110 includes a reservoir 112 which contains a quantity of analyte calibrant 114. The device 110 includes a body or housing 116 having a plurality of intersecting conduits or bores 118, 120 and 122. The bore 118 includes first and second sections 119, 121, respectively, and extends substantially through the housing 116. The bore 120 extends to the bore 118 and is in flow communication with an outlet nozzle 124. A bore 126 connects the bores 118 and 120, and defines a dosing chamber 128. The dosing chamber 128 will store a predetermined volume of calibrant 14, with the predetermined or desired amount being determined by the internal volume of the dosing chamber 128.

A bore 130 connects the bore 122 with the dosing chamber 128, and an air supply inlet 132 intersects the bore 122. The air supply inlet 132 is connected to a source of pressurized air, which is supplied from a supply source at approximately 3 psig. The device 110 includes a valving mechanism 134 having a first valve 142 disposed in the section 121 of the bore 118 and further having a tip 144 adapted to close off the outlet end 138 of the dosing chamber 128. The valve mechanism 134 also includes a second valve 146 disposed in the bore 122 and having a tip 148 adapted to close off an inlet end 150 of the bore 130. The valving mechanism 134 is operable in a manner similar to that described above with respect to the first preferred embodiment.

The dosing chamber 128 includes an input end 136, an output end 138, and an intermediate portion 140. The bore 130 intersects the dosing chamber 128 at the intermediate portion 140. The bore 18 includes a section 139, with the section 139 being disposed adjacent the input end 136 of the dosing chamber 128. The section 139 has a diameter greater than the diameter of the dosing chamber 128, such that the section 139 functions as a pneumatic restriction. Although the bore 118 is shown as having two sections of different diameter, the bore 118 alternatively may be of uniform diameter, as long as the cross-sectional area of the section 139 immediately adjacent to the input end 136 of the dosing chamber 128 is significantly greater than the cross-sectional area of the dosing chamber 128. This difference in cross-sectional area ensures that the volume of calibrant disposed in the section 139 of the bore 118 immediately adjacent to the input end 136 of the dosing chamber 128 is significantly greater than the volume of calibrant stored in the dosing chamber 128. Accordingly, in response to the operation of the valving mechanism 134 and the introduction of the actuation pressure to the calibrant 114 stored in the dosing chamber 128, the calibrant 114 will follow the path of least pneumatic resistance and will thus be ejected from the outlet nozzle 124.

It will be understood that in either of the above-discussed embodiments, the reservoir may instead be piping system containing a process stream of a fluid material, and the device may be employed to periodically sample the purity or the constituency of the process stream by ejecting a known quantity of the fluid material to a sensing device.

It will further be understood that the above description does not limit the invention to the above-given details. It is contemplated that various modifications and substitutions can be made without departing from the spirit and scope of the following claims.

What is claimed:

1. A leak sensor calibration device, comprising:

a reservoir for sotring a calibrant;

a conduit in flow communication with the reservoir, the conduit including a bore;

an insert sized for insertion into the bore, the insert defining a dosing chamber for storing a measured quantity of the calibrant, the dosing chamber defined exclusively by a T-shaped bore in the insert;

an outlest nozzle in flow communication with the dosing chamber;

an air supply source adapted to pressureized the measured quantity of calibrant stored in the dosing chamber; and a valve mechanism adapted to eject the measured quantity of calibrant stored in the dosing chamber to the atmosphere through the outlet nozzle, wherein the valve mechanism includes a first valve disposed between the dosing chamber and the outlet nozzle, the first valve being shiftable between a closed position and an open position, the first valve in the further including a second valve disposed between the air supply source and the dosing chamber, the second valve being shiftable between a closed position and an open position, the second valve in the closed position isolating the air supply source from the dosing chamber.

2. The device of claim 1, wherein the first and second valves are electrical remotely operable valves, and further including a controller for remotely operating the first and second valves.

3. The device of claim 2, wherein the controller moves the first valve to the open position for a first predetermined time interval and moves the second valve to the open position for a second predetermined time interval, the second time interval being less than the first time interval and being equal to the predetermined duration, the second time interval occurring during the first time interval.

4. The device of claim 3 wherein the first time interval is 50 milliseconds and wherein the second time interval is 10 milliseconds.

5. The device of claim 3, wherein the controller moves the second valve to the open position for a third predetermined time interval, the third time interval occurring prior to the first and second time intervals.

6. The device of claim 1, including a check valve disposed between the dosing chamber and the reservoir, the check valve being shiftable between an open position and a closed position, the check valve being shifted toward the closed position in response to movement of the second valve toward the open position.

7. A leak sensor calibration device, comprising:

a reservoir for storing a calibrant;

a conduit in flow communication with the reservoir, a portion of the conduit defining a dosing chamber for storing a measured quantity of the calibrant, a second portion of the conduit defining a second chamber immediately adjacent to the dosing chamber, a diameter of the second chamber greater than a diameter of the dosing chamber such that the second chamber defines a restrictor, the restrictor defined exclusively by a volume of the second chamber, the second chamber holding a second quantity of the calibrant greater than the measured quantity of the calibrant;

an outlet nozzle in flow communication with the dosing chamber;

an air supply source adapted to pressurize the measured quantity of calibrant stored in the dosing chamber; and a valve mechanism adapted to eject the measured quantity of calibrant stored in the dosing chamber directly to the atmosphere through the outlet nozzle, the valve mechanism further being adapted to eject the measured quantity in a burst having a predetermined duration.

* * * * *

UNITED STATES PATENT AND TRADEMARK OFFICE
CERTIFICATE OF CORRECTION

PATENT NO.    : 6,408,674 B1  Page 1 of 1
DATED         : June 25, 2002
INVENTOR(S)   : John P. Dilger It is certified that error appears in the above-identified patent and that said Letters Patent is hereby corrected as shown below:

<u>Column 7,</u>
Line 49, delete "outlest" and insert -- outlet --.

Signed and Sealed this

Fourteenth Day of January, 2003

JAMES E. ROGAN
*Director of the United States Patent and Trademark Office*